United States Patent [19]

Garth et al.

[11] Patent Number: 5,163,941
[45] Date of Patent: Nov. 17, 1992

[54] INTUBATION DEVICE

[75] Inventors: Geoffrey C. Garth, Long Beach; Charles A. Patterson, Westminster, both of Calif.

[73] Assignee: California Medical Products, Long Beach, Calif.

[21] Appl. No.: 696,841

[22] Filed: May 7, 1991

[51] Int. Cl.⁵ ............................................. A61M 16/00
[52] U.S. Cl. .................................. 606/108; 604/165; 24/518; 24/520
[58] Field of Search ................ 606/108; 604/281, 165, 604/164, 158, 282, 283; 128/4-11, 395-398, 207.14-207.16; 24/16 PB, 17 AP, 19, 499, 517, 518, 520

[56] References Cited

U.S. PATENT DOCUMENTS

| | | |
|---|---|---|
| D. 240,322 | 6/1976 | Staub . |
| 1,883,041 | 10/1932 | Somers ........................ 24/517 X |
| 2,541,402 | 2/1951 | Caine . |
| 2,693,182 | 11/1954 | Phillips . |
| 2,888,017 | 5/1959 | Wallace ......................... 128/7 X |
| 3,881,468 | 5/1975 | Foltz . |
| 4,185,639 | 1/1980 | Linder . |
| 4,193,174 | 3/1980 | Stephens .................... 606/108 X |
| 4,315,505 | 2/1982 | Crandell et al. ........... 128/207.15 X |
| 4,337,763 | 7/1982 | Petrassevich ................ 128/11 X |
| 4,444,185 | 4/1984 | Shugar .......................... 128/11 X |
| 4,449,522 | 5/1984 | Baum . |
| 4,567,882 | 2/1986 | Heller ............................. 128/11 |
| 4,681,094 | 7/1987 | Rolnick ......................... 128/10 |
| 4,685,457 | 8/1987 | Donenfeld . |
| 4,690,138 | 9/1987 | Heyden . |
| 4,747,827 | 5/1988 | Micek ............................ 604/281 |
| 4,834,709 | 5/1989 | Banning et al. ................ 604/281 X |
| 4,838,880 | 6/1989 | Honma ........................ 24/499 X |
| 4,840,172 | 6/1989 | Augustine et al. . |

OTHER PUBLICATIONS

"Early Experience With Illuminated Endotracheal Tubes in Premature and Term Infants", article by Richard M. Heller, M.D., et al. *Pediatrics*, Apr. 1, 1985, vol. 75, No. 4, pp. 664–666.

Device For Blind Nasal Intubation article, *Anesthesiology*, Mar.-Apr. 1959, vol. 20, p. 221.

Article in *Anesthesiology*, May-Jun. 1959, vol. 20, pp. 382-382 re Maleable stylet.

*Primary Examiner*—Peter A. Aschenbrenner
*Attorney, Agent, or Firm*—Pretty, Schroeder, Brueggemann & Clark

[57] ABSTRACT

An intubation device and a method of intubating a patient with an endotracheal tube is disclosed. The device comprises a housing and a flexible, tubular sheath having one end connected to the housing and a free end extending away from it. The sheath, which is adapted to fit within the endotracheal tube, also has a special light at the end of the sheath's free end for selectively providing illumination. In use, the sheath is inserted into the endotracheal tube until the light is at the end of the distal end of the tube. A clamp on the intubation device then clamps the endotracheal tube to the housing to prevent relative movement between the tube and the sheath. A tube stop is then slid along the sheath into abutting contact with the proximal end of the endotracheal tube to identify the location on the sheath corresponding to the proximal end of the tube. When the tube is properly positioned in the patient, the light will create a distinct glow visible to an observer in the area of the sternal notch. Thus, when it is desired to confirm or recheck placement of the endotracheal tube in the patient, the sheath may be simply inserted into the tube until the proximal end of the tube contacts the tube stop. The device also includes a trocar wire for insertion into the sheath to provide added stiffness.

34 Claims, 7 Drawing Sheets

INTUBATION DEVICE

BACKGROUND OF THE INVENTION

The present invention relates to intubation devices and, more particularly, to a device and method for inserting and checking the placement of an endotracheal tube in a patient.

Certain types of illness and injury can cause a patient's airway to become blocked or otherwise impaired, preventing adequate oxygenation and ventilation of the patient. When this occurs, prompt corrective action must be taken. Often times, this action requires the placement of an endotracheal tube in the patient's trachea in order to restore or maintain an adequate airway. The process of inserting the tube in the patient is commonly referred to as intubation.

Over the years, various types of intubation devices have been developed for inserting endotracheal tubes in a patient. Perhaps the most commonly used intubation technique is a process known as direct laryngoscopy. In this technique, a device called a laryngoscope is used to actually visualize the upper airway through the patient's mouth during the process of inserting the endotracheal tube. This technique is usually successful in ensuring correct placement of the tube in most patients. However, direct laryngoscopy is not feasible under all circumstances. Indeed, performing intubation on a relaxed, well-prepared patient in a hospital setting is much different than attempting to intubate an accident victim in a moving ambulance, helicopter or on the street itself. Moreover, direct laryngoscopy can have the disadvantage of increasing the risk of dental and soft tissue trauma under certain circumstances.

When intubation is properly performed, regardless of the procedure employed, the inserted end of the endotracheal tube will be positioned in the patient's trachea at a location substantially between the patient's vocal cords and carina. This location has been found to provide the best and most reliable airway management for several reasons. If the tube is not inserted far enough past the vocal cords, for example, it can become dislodged and ineffective, such as when it ends up in the esophagus. If the tube is inserted too far into the trachea, however, past the carina, then the tube may only function to adequately ventilate one of the lungs, instead of both. This can lead to serious complications of its own. Thus, proper placement of the inserted end of the tube plays a major role in the intubation process.

Various techniques have been used in the past to attempt to ensure that the endotracheal tube lies in the proper location between the patient's vocal cords and carina at the end of the intubation process. One such technique involves placing a light at the inserted end of the endotracheal tube prior to intubation. The technique is based on the principle of transillumination, that a strong light can be transmitted through the cartilage and soft tissues of the neck. It was further discovered that when the light at the end of the tube was clearly visible through the patient's skin in the area of the sternal notch, then the inserted end of the tube was approximately halfway between the vocal cords and carina in most patients. The absence of a clear glow of illumination in this area usually indicates incorrect placement, such as in the esophagus.

Eventually, so-called lightwands were developed for use in the intubation process. Early lightwands comprised either a rigid or flexible copper wire with a battery at one end and a light at the other. When a rigid wire was used, it functioned as a stylet to stiffen and guide the tube into the trachea. The flexible wire typically has been used for nasotracheal intubation. Later lightwands were somewhat more sophisticated but not different in function.

While the development of the lightwand has been helpful in visualizing the airway during intubation and ensuring proper placement of the tube, the intubation technique still suffers from certain disadvantages. For example, sometimes the lightwand will become jarred or bumped during intubation and move from its position at the end of the tube. In these circumstances, the intubation procedure must be aborted and restarted, with the light at the proper location.

Moreover, once the lightwand is withdrawn from the tube after correct placement, there has been no reliable way to recheck the position of the tube at a later time. It has been known to use end-tidal $CO_2$ measurements to monitor proper ventilation in an attempt to confirm, without visual evidence, that the tube is still in the trachea and not the esophagus. However, endtidal $CO_2$ equipment may not be readily available, and patients in shock or in cardiac arrest may not be good candidates for qualitative measuring devices. Additionally, end-tidal $CO_2$ measurements usually cannot detect right mainstem bronchial position, which can be a significant complication.

Other problems with known lightwands include the fact that the lights are directed in a forward manner such that the light tends to shine into the airway, rather than toward the patient's sternal notch. This makes the light difficult to see, unless the procedure is conducted in relatively low light conditions. This is especially true when intubation is being performed in bright sunlight, despite attempts to shield the patient's skin. As a result, proper placement of the tube cannot be readily confirmed, thus risking injury to the patient.

Still another problem with prior lightwands has been found to reside in the type and location of the switch used to illuminate the light. For example, the location of some switches has required that a second hand rotate the switch to the "on" position. This is time consuming, troublesome and inconvenient at best.

Accordingly, there has existed a definite need for an intubation device that ensures reliable and accurate placement of an endotracheal tube in a simple and convenient manner. There further has existed a need for an intubation device which, after intubation has been accomplished, enables fast and reliable checking of the tube placement at a later time. Finally, there has existed a need for an intubation device that can be operated using a single hand to intubate and illuminate the light, leaving the second hand free for other uses. The present invention satisfies these needs and provides further related advantages.

SUMMARY OF THE INVENTION

The present invention provides an intubation device for use with an endotracheal tube to be inserted into a patient's trachea to provide proper oxygenation and ventilation of the patient. Insertion of the tube is facilitated by a special light on the device which is positioned at the inserted end of the endotracheal tube to help illuminate the airway and provide a distinct glow that is highly visible on the outer surface of the neck, which allows for monitoring of the tube's position. When the glow is seen at the patient's sternal notch, it indicates correct placement of the tube in the trachea, between the patient's vocal cords and carina. The device also includes a unique tube clamp and a tube stopping feature that enables fast and reliable checking of the tube placement at a later time. The intubation device of the present invention furthermore is intended to be reliable in operation, simple to use, ideally with only one hand, and is relatively inexpensive to manufacture.

More particularly, the intubation device comprises an elongated housing for manual grasping and a flexible, tubular sheath having one end connected to the housing and a free end extending away from the housing. In use, the sheath is inserted into the endotracheal tube until a light at the sheath's free end is located at the inserted end of the tube. When the light is at this location relative to the tube's inserted end, a tube clamp on the housing is closed to secure the endotracheal tube to the housing, thereby preventing relative movement between the sheath and the tube.

The intubation device also includes a special tube stop designed to slide along the sheath into abutting contact with the exposed or uninserted end of the endotracheal tube. Thus, when the sheath has been inserted into the tube to a location where the light is located at the end of the inserted end of the tube, the tube stop may be moved into abutting contact with the exposed end of the tube and thereafter secured to the sheath. In this way, the appropriate depth of insertion of the sheath within the endotracheal tube can be consistently and reliably identified at a later time. After the tube stop has been secured to the sheath, the clamp may be released and the sheath removed from the endotracheal tube so that ventilation equipment can be connected to the tube in the usual manner. Later, when it is desired to recheck or confirm the location and placement of the tube in the trachea, the sheath may be simply inserted into the tube until the tube stop abuts the exposed or uninserted end of the tube. After fully inserting the sheath to this point, the light at the free end of the sheath will be at the inserted end of the tube, as before. Thus, the proper location and placement of the tube in the patient's trachea may be verified by illuminating the light and looking for illumination through the patient's skin in the area of the sternal notch. Finding such illumination will confirm proper placement of the tube between the patient's vocal chords and carina.

In one aspect of the invention, the tube clamp comprises a tube holder connected to the housing having a curved portion facing the tube. Within this curved portion, a resilient, flexible band is positioned such that one end of the band is connected to one side of the curved portion, with the other end of the band resting against the opposite side of the curved portion, so that at least an intermediate portion of the band is spaced from the curved portion. A clasp pivotally connected to the tube holder has a curved section for clamping the tube down against the flexible band and against the curved portion of the tube holder. When the clasp is released, however, the endotracheal tube springs away from the tube holder, and the flexible band springs up moving the clasp to a position well out of the way so as to not interfere with the removal of the device from the tube. This makes it easier to remove the sheath from the tube after insertion.

The tube clamp is designed so that it will adequately receive and secure a variety of different sized endotracheal tubes. This is accomplished by using the flexible band and the pivotal clasp, noted above, which is preferably secured to the tube holder in a snap-fit manner. For large size endotracheal tubes, the flexible band is forced tightly against the curved portion of the tube holder when the clasp is secured. For smaller size tubes, however, the flexible band will bend, but it will not be completely forced against the curved portion of the tube holder. To help prevent sliding movement of the tube within the tube clamp for smaller size tubes, a friction enhanced surface on the flexible band is provided. In one embodiment, the flexible band is made of metal and the friction enhanced surface comprises protrusions adapted to bite into the outer surface of the endotracheal tube.

In another aspect of the invention, the intubation device further comprises a trocar wire for insertion inside the sheath to stiffen the sheath and facilitate the intubation process. The wire preferably is comprised of a ductile or malleable material such that the wire and sheath may be bent and maintained at varying angles. Insertion and withdrawal of the wire from the sheath is facilitated by making the sheath of a material, such as teflon, having a low coefficient of friction. Rotation of the wire with respect to the sheath also is prevented by providing a notch on the housing which the wire engages after it has been inserted into the sheath.

In other aspects of the invention, the light at the sheath's free end comprises a special light having a reflector that directs a portion of the light's illumination substantially to one side of the sheath. In this way, an increased amount of illumination from the light will be directed toward the surface of the skin at the patient's sternal notch when the device is properly used. This makes the light much easier to see, especially when intubation is being performed in bright light.

A special switch also may be optionally provided on the housing for controlling illumination of the light. The switch comprises a slide switch moveable to an on position for turning the light on and an off position for turning the light off. A button switch also is provided to selectively provide pulses of illumination. Thus, when the slide switch is in the off position, the button switch may be depressed to turn the light on. However, when the slide switch is in the on position, depression of the button switch will turn the light off. By pulsing the light during intubation, the progress of the endotracheal tube can be monitored more easily when the ambient light levels are high. Pulsing the light when rechecking tube placement also provides a more visible illumination for reference purposes.

By placing the inserted end of the endotracheal tube in the patient's mouth and up against the cheek prior to inserting the tube into the trachea, and by illuminating the light against the cheek, the light visible through the patient's cheek will provide a reference degree of illumination. This reference degree of illumination has been found to be substantially the same as the degree of illumination visible through the cartilage and soft tissues of the neck in the area of the patient's sternal notch (i.e., between the patient's vocal cords and carina) when the light has been properly placed in the trachea. Periodically, illuminating the light or leaving it on while inserting the tube into the patient's trachea will allow the location of the inserted end of the tube to be monitored during its insertion. Insertion of the tube into the trachea is stopped when substantially the same reference degree of illumination is visible in the area of the sternal notch.

Other features and advantages of the present invention will become apparent from the following detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
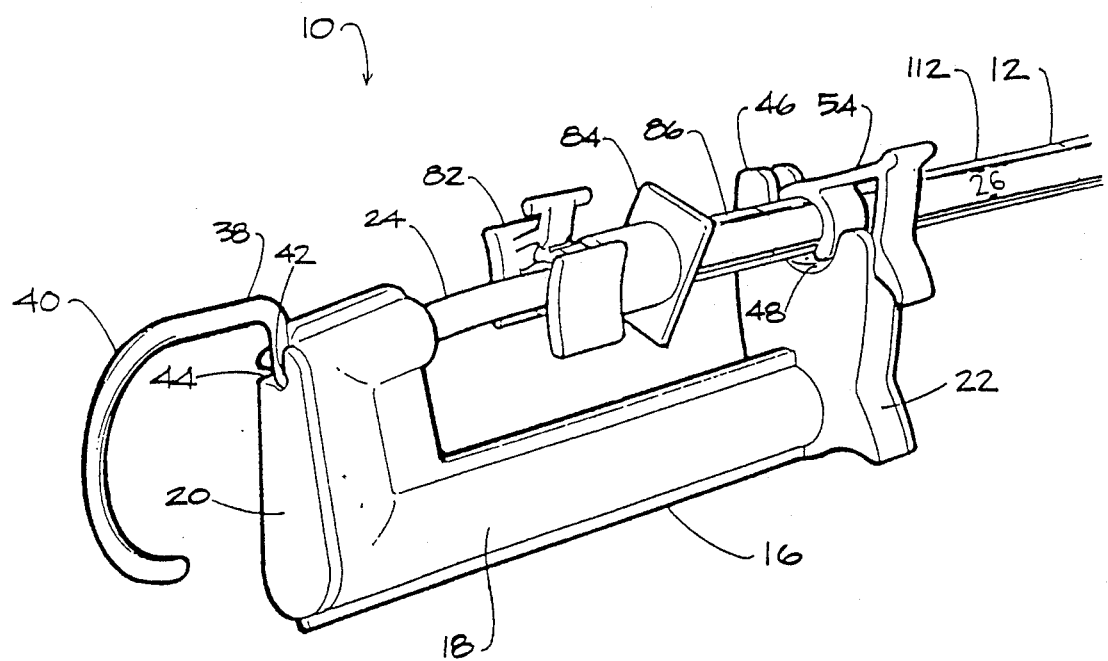
FIG. 1 is a partial perspective view of an intubation device embodyinq the novel features of the present invention, showing the device ready for use with an endotracheal tube.

As shown in the exemplary drawings, the present invention is embodied in an intubation device, generally referred to by the reference numeral 10, for use in inserting an endotracheal tube 12 into a patient to provide adequate ventilation and oxygenation of the patient. The device 10 is advantageously designed for orotracheal or nasotracheal intubation, as well as for subsequent confirmation of the placement and position of in-place tubes. These and other features and advantages of the invention are described in detail below.

Figure 8:
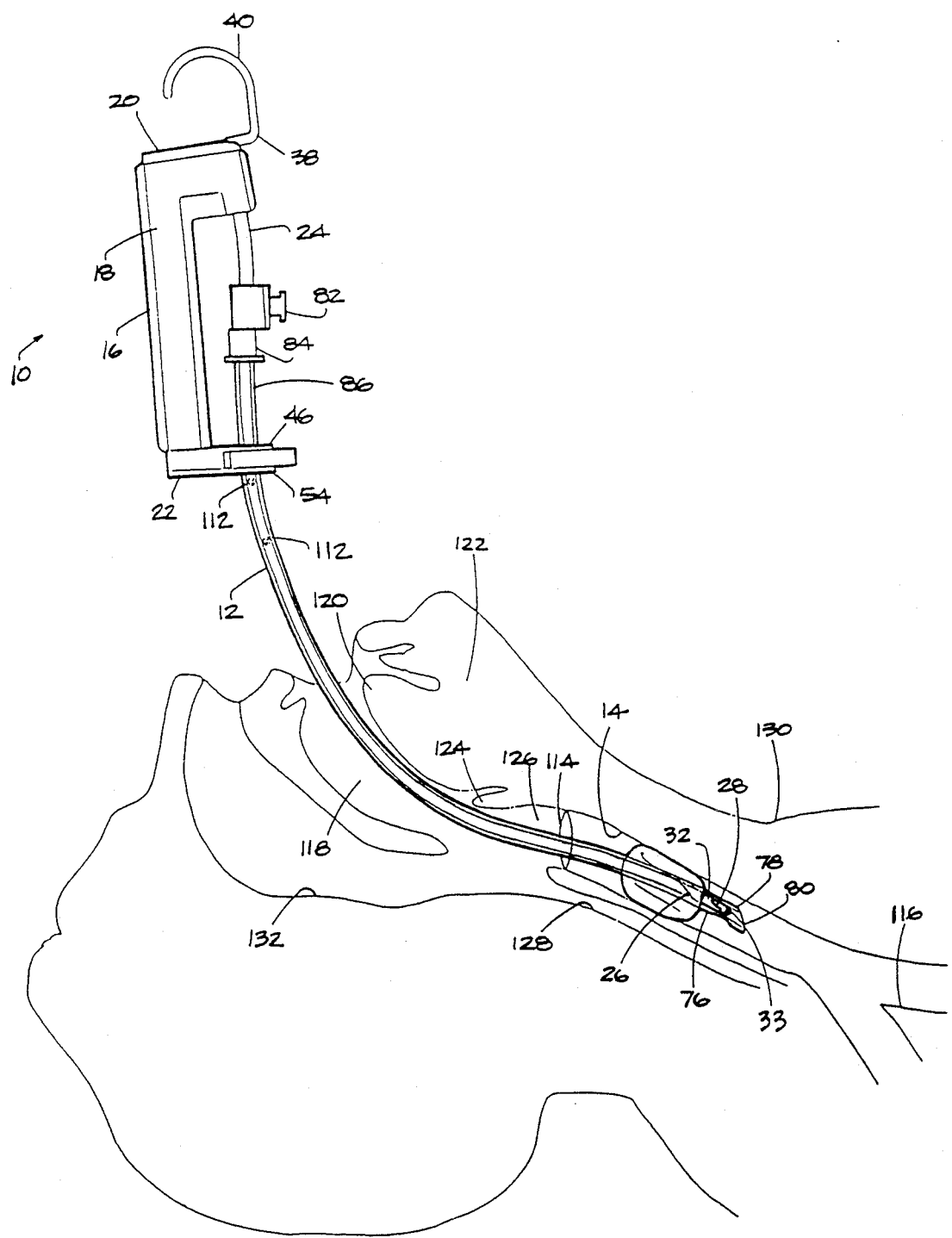
FIG. 8 is an elevational view of the intubation device, showing use of the device for orotracheal intubation.
Figure 9:
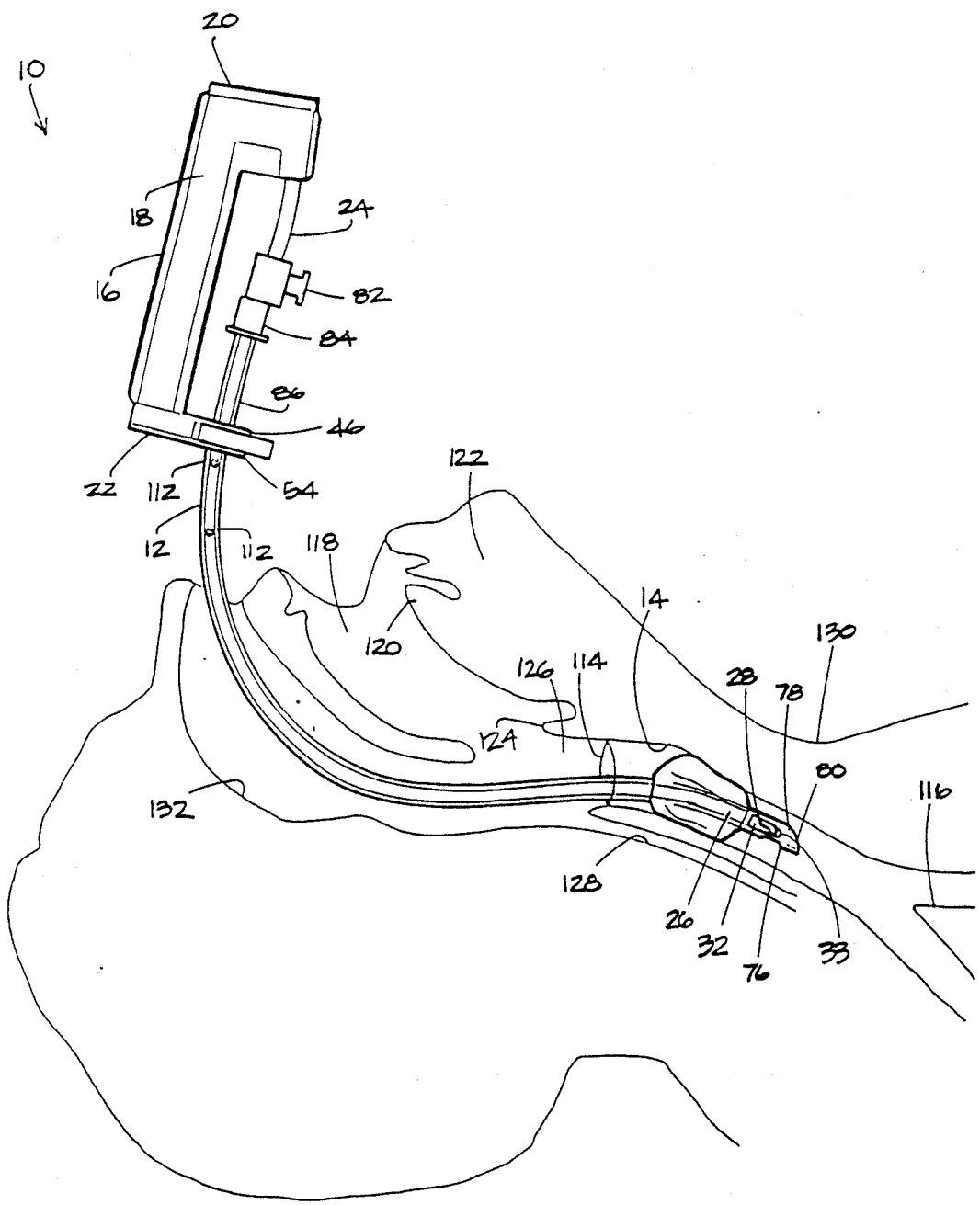
FIG. 9 is an elevational view of the intubation device, similar to FIG. 8, showing use of the device for nasotracheal intubation.

FIG. 1 shows the device 10 connected to the tube 12 and ready for insertion into the patient's trachea 14 (FIGS. 8-9). The device 10 comprises a housing 16 having a generally cylindrical body 18 with an extension 20 at one end and a tube holder 22 at the other end. The extension 20 connects one end of an elongated, tubular sheath 24 to the housing 16 so that the sheath overlies the tube holder 22 and is substantially parallel to the housing's cylindrical body 18. The sheath 24 is preferably made of a flexible plastic material to enable relatively free bending and manipulation of the sheath.

Figure 2:
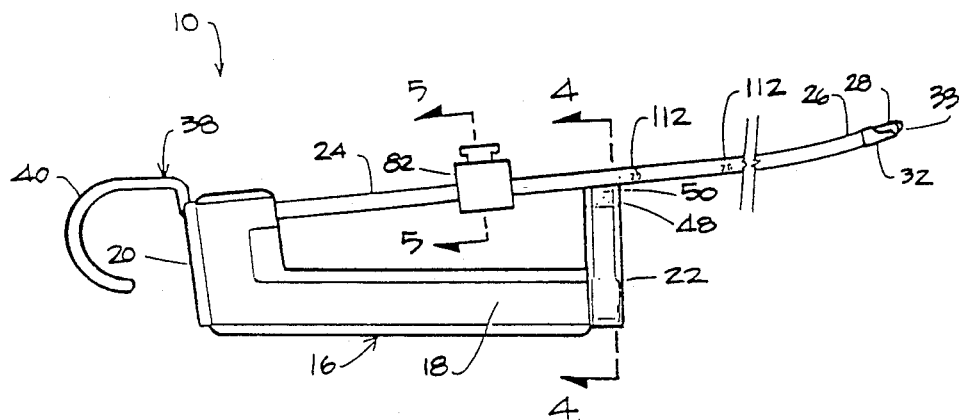
FIG. 2 is a right side elevational view of the intubation device, shown with the endotracheal tube removed.
Figure 3:
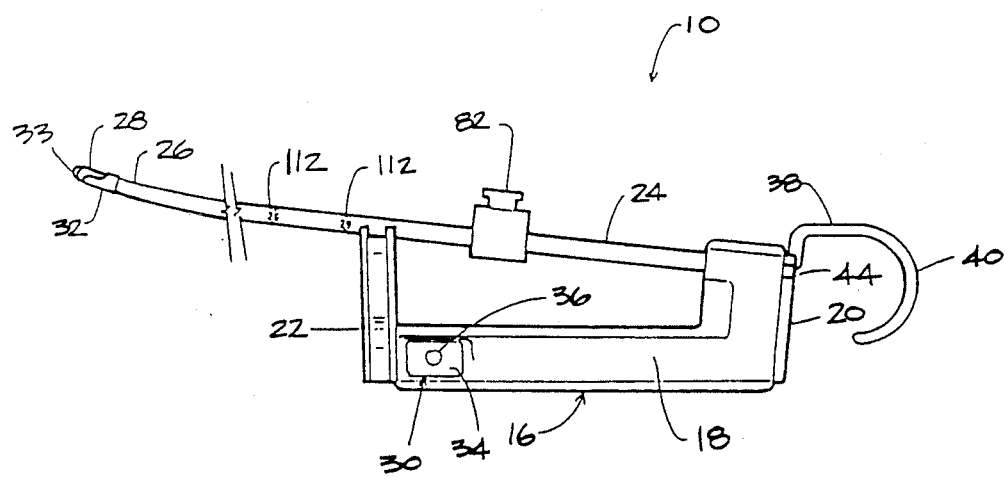
FIG. 3 is a left side elevational view of the intubation device, similar to FIG. 2.

FIGS. 2-3 show elevational views of the intubation device 10, with the endotracheal tube 12 omitted for purposes of clarity. It is noted here that the sheath 24 is connected to the housing 16 so that the sheath extends upwardly at a slight angle relative to the housing's cylindrical body 18. This causes the sheath 24 to be slightly spaced from the tube holder 22. The significance of this spacing of the sheath 24 is explained in more detail below.

As shown best in FIG. 3, the free end 26 of the sheath 24 which is not connected to the housing 16 includes a special light 28 that may be selectively illuminated by operating a switch 30 on the housing. The light 28 in the preferred embodiment comprises a filament type bulb that has a reflector shield 32 on its backside to reflect a substantial portion of the light's illumination to one side of the sheath 24. The reflector shield 32 may be located outside the bulb 28 and covered by a portion of the sheath, shrink wrap tubing or the equivalent to facilitate cleaning of the sheath and bulb, and to prevent the reflector shield 32 from separating from the light bulb 28. The bulb 28 also includes a lens 33 to focus a portion of the illumination in a direction in which the free end 26 of the sheath 24 is pointing. The bulb 28 is powered by batteries (not shown) in the cylindrical body 18 of the housing 16, and the electrical connection between the batteries and the bulb can be accomplished using conventional conductors 35 (FIGS. 5-6) carried within the sheath 24.

The directional nature of the light bulb 28 advantageously directs a substantial portion of the illumination from the bulb to one side of the sheath 24. This is an important feature, since the bulb's illumination will be directed toward the patient's anterior tracheal wall and thus the outside skin for visualization by the user. The reflected illumination also will be more distinct and concentrated, about twice the normal unreflected illumination, making it easier to see, especially when ambient light is relatively strong. This is a notable improvement over prior designs, in which the illumination was unreflected and tended to shine down into the airway, thereby producing a less distinctive and less visible transilluminated glow. Nevertheless, it is still desirable to have an adequate amount of illumination directed toward the airway. The lens 33 satisfies this illumination need by focusing a portion of the bulb's illumination in this direction.

The switch 30 for controlling illumination of the bulb is shown in FIG. 3. The switch 30 comprises a slide switch 34 for manual movement by one's finger to an "on" or an "off" position to respectively connect and disconnect electrical power to the bulb 28. In the "on" position, the bulb 28 is illuminated continuously, and in the "off" position the bulb is not illuminated.

The slide switch also may optionally include a button switch 36 that may be depressed to provide pulses of illumination, with the slide switch 34 in either the "on" or "off" position. When the slide switch 34 is in the "on" position and the bulb 28 is illuminated, depression of the button switch 36 will disconnect electrical power to the bulb for as long as the button switch is depressed. Depressing the button switch 36 therefore turns the light 28 off, while releasing it allows the light to go back on again. Similarly, when the slide switch 34 is in the "off" position and the bulb 28 is not illuminated, depression of the button switch 36 will connect electrical power to the bulb for as long as the button switch is depressed. Depressing the button switch 36 therefore turns the light on, while releasing it allows the light to go back off again. Hence repeated, sequential depression of the button switch 36 at any time, with the slide switch 34 in either the "on" or "off" position will produce pulses of illumination by the bulb 28.

It will be appreciated that the bulb 28 can generate relatively high temperatures when it is illuminated for an extended period of time. Pulsing of the bulb 28, as described above, should help to significantly reduce heat build-up and high temperatures. The heat that is produced by the bulb 28 should not pose a problem in any event, in view of the heat exchanging nature of the upper airway, and because use of the intubation device 10 of the present invention, as described below, does not involve contact between the bulb 28 and the patient's tissue.

With further reference to FIGS. 1-3, the intubation device 10 further includes a trocar or stylet 38 in the form of a thin wire that is received within a hollow shaft in the sheath 24. The trocar wire 38 preferably is made of a ductile or malleable material that is capable of being bent and maintained at varying angles. When inserted in the sheath 24, the trocar wire 38 provides added stiffness to the sheath to facilitate orotracheal intubations. It also allows the free end 26 of the sheath 24 to be bent at an angle to further facilitate intubation. When the trocar wire 38 is removed, the sheath 24 is very pliable and easily conforms to the anatomy of the upper airway. Hence, the trocar wire 38 is not used in nasotracheal intubations.

Figure 7:
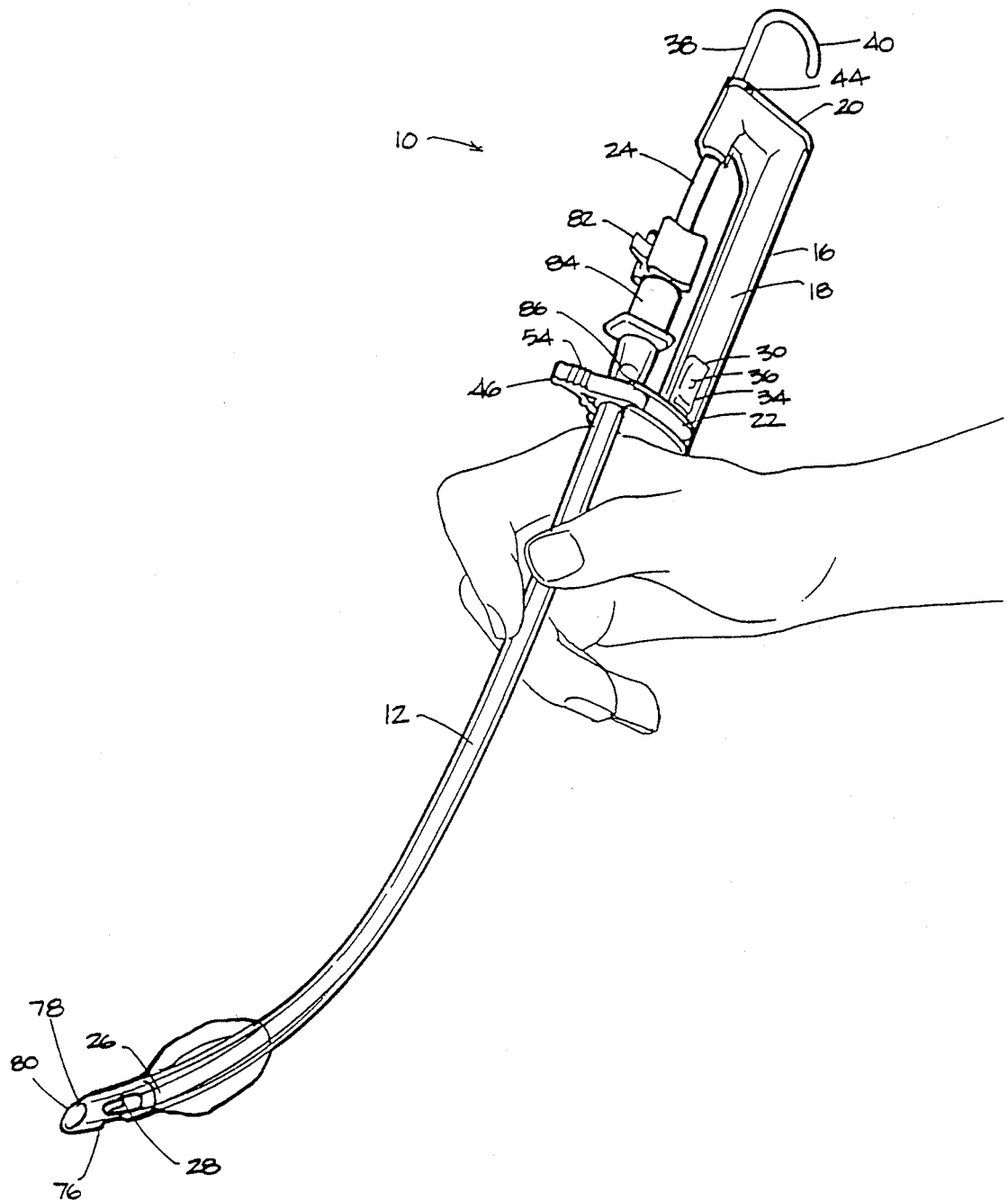
FIG. 7 is a perspective view of the intubation device, showing one preferred manner of holding the device and tube for intubation purposes.

During intubation using the trocar wire 38, the sheath's free end 26 is usually bent in the shape of a hockey stick, as shown in FIG. 7. To maintain this shape, the trocar wire 38 should not rotate inside the sheath 24. To prevent such rotation, the trocar wire 38 is provided with a curved handle 40 that is received within one of two notches 42 and 44 formed in the extension 20 of the housing 16. Thus, when the trocar wire 38 is fully inserted into the sheath 24, the handle 40 will fit within one of the notches 42 and 44 (FIG. 1). Two notches 42 and 44 are provided in the preferred embodiment to allow the handle 40 to assume two different positions, each at ninety degree angles to each other, depending upon the preference of the user. For example, some users will prefer to have the handle 40 at the orientation shown in FIG. 1, while others may prefer the handle to be in a different orientation by ninety degrees. This preference for handle orientation usually is dictated by the particular intubation technique adopted by the user and the positioning of one's hand relative to the handle 40 to withdraw the trocar wire 38 from the sheath 24 during the intubation process. In any event, the location of the trocar wire 38 and its variable orientation help to simplify the intubation procedure and ensure single handed use.

The trocar wire 38 typically is withdrawn from the sheath 24 midway during an orotracheal intubation. In this regard, it is important that the wire 38 be withdrawn smoothly and as easily as possible to prevent tissue trauma. Accordingly, the hollow shaft of the sheath 24 preferably is lined with a material having a low coefficient of friction. In the preferred embodiment, this material comprises teflon, which may be used to construct the entire sheath 24 and not just the lining of the sheath's hollow shaft. The trocar wire 38 also may be coated with a material having a low coefficient of friction, such as teflon, to further facilitate insertion and withdrawal of the wire.

Figures 4A, 4B:
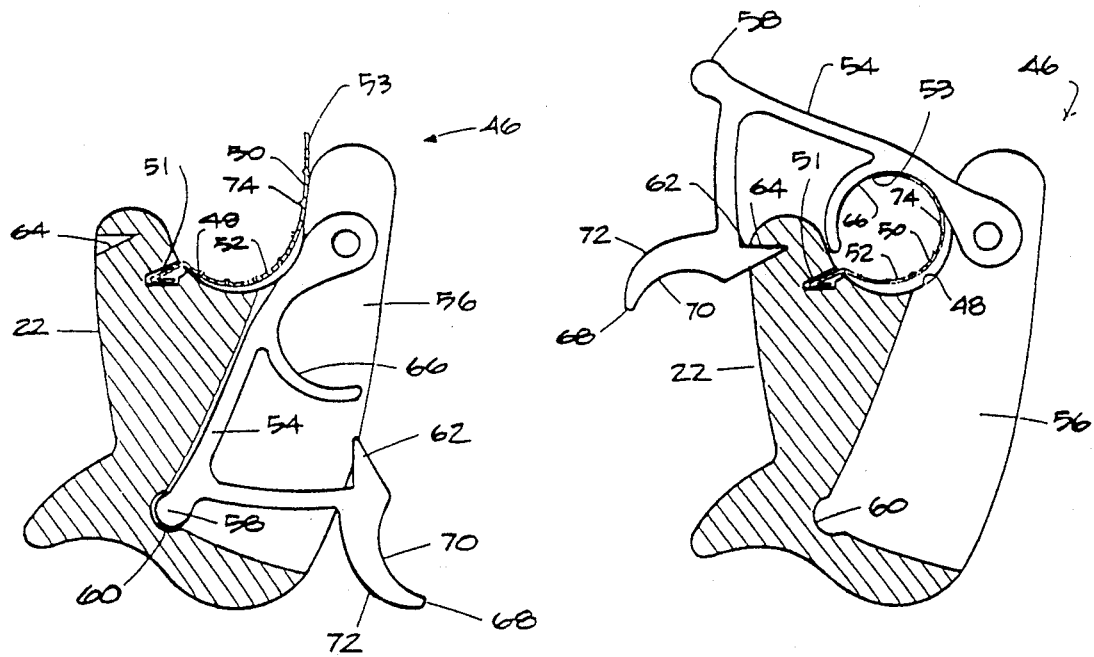
FIGS. 4A-4B are cross-sectional views of a tube clamp of the intubation device, taken substantially along line 4—4 of FIG. 2, showing the clamp in open and closed positions, respectively.

The intubation device 10 also includes a tube clamp 46 for clamping the endotracheal tube 12 to the housing 16 after the sheath 24 has been inserted into the tube. Thus, the tube clamp 46 prevents relative movement between the tube 12 and the sheath 24, which is very important to the success of the intubation process. As shown best in FIGS. 4A-4B, the tube clamp 46 is connected to the forward end of the housing 16 and comprises the tube holder 22, which has a curved portion 48 facing the overlying endotracheal tube 12 (FIG. 1). A flexible band 50 overlies the curved portion 48 and has one end 51 secured to one side of the curved portion and another end 53 that rests against the opposite side of the curved portion where it extends upwardly beyond the curved portion. The band 50 also is configured so that an intermediate section 52 of the band 50 is spaced from the curved portion 48. This arrangement allows the band 50 to have the properties of a spring, in that depressing the end 53 will move the intermediate section 52 toward the curved portion 48 of the tube holder 22, while releasing it will cause the intermediate section to spring back to its original state, as shown in FIG. 4A.

The tube clamp 46 further comprises a clasp 54 having one end pivotally connected to the tube holder's curved portion 48 on the same side as the band end 53. This pivotal connection allows the clasp 54 to pivot between a clamped and unclamped position with respect to the tube holder 22. In the unclamped position, shown in FIG. 4A, the clasp 54 is received within a recess 56 of the tube holder 22. Here, the clasp 54 is completely out of the user's way and there is no risk of it catching on anything. To ensure that the clasp 54 remains secured in the unclamped position, a bead 58 on the clasp 54 is adapted to snap-fit within a groove 60 in the recess 56. In the clamped position, shown in FIG. 4B, the clasp 54 has a finger 62 which is received in a snap-fit engagement with a notch 64 on the other side of the tube holder's curved portion 48, opposite the side where the clasp 54 is pivotally connected to the tube holder 22. Here, the clasp 54 is completely closed and locked in place, such that a curved section 66 on the clasp 54 overlies the curved portion 48 of the tube holder 22 to form a substantially cylindrical clamp. Closing of the clasp 54 also contacts the band end 53 causing it to conform to the curvature of the clasp's curved section 66 (FIG. 4B).

A tab 68 also is provided on the tube clamp 46, having a concave configuration 70 on one side and a convex configuration 72 on the other. The tab's concave configuration 70 facilitates unsnapping of the clasp 54 when it is in the closed position and pushing the bead 58 into the groove 60, thereby securing the clasp 54 in the unclamped position. The tab's convex configuration 72 facilitates moving the bead 58 out of the groove 60 and snapping the finger 62 into the notch 64, thereby securing the clasp 54 in the clamped position.

The tube clamp 46 described above has many advantages. One very significant advantage is that when the clasp's finger 62 is released from the notch 64, the end 53 of the band 50 will urge against the clasp's curved section 66 and cause the clasp 54 to rapidly pivot away from the tube 12. As noted previously, the sheath 24 is connected to the housing 16 at a slight upward angle relative to the housing's cylindrical body 18. Thus, the angular orientation of the sheath 24 with respect to the housing 16 also tends to eject the tube 12 away from the tube holder 22 and to maintain the tube in a spaced relation from it when the clasp 54 is released. The combination of these features advantageously allows free and unrestricted access to the endotracheal tube 12, without interference by the tube holder 22, clasp 54 or other structure of the intubation device 1 to facilitate the rapid and easy removal of the device from the endotracheal tube.

Another important advantage of the tube clamp 46 is its ability to receive and clamp various size endotracheal tubes. The clamp 46 presently is adapted to receive size 7, 8 and 9 tubes. When clamping large size tubes, such as size 9, the clasp 54 is firmly moved to the closed position and the flexible band 50 is forced down very tightly against the curved portion 48 of the tube holder 22. When clamping small size tubes, such as size 7, it will be easier to snap the clasp 54 to the closed position and the flexible band 50 will bend, but it normally will not be forced all the way against the curved portion 48 of the tube holder 22.

To help prevent slippage between the tube clamp 46 and the endotracheal tube 12, the flexible band 50 is provided with a friction enhanced surface. In the preferred embodiment, for example, the band 50 is made of metal and the friction enhanced surface comprises a plurality of protrusions 74 on the band that are designed to bite into the outer surface of the tube 12 when the clasp 54 is in the clamped position. It will be appreciated that other types of friction enhanced surfaces may be used to inhibit slippage between the clamp 46 and tube 12.

It is also noted that the clasp 54 can be conveniently and quickly moved to the closed position for any size tube with one simple movement that secures the finger 62 on the clasp 54 within the notch 64 on the tube holder 22. This has advantages over multiple notch devices, where a different notch corresponds to a different sized tube. It can be seen that use of a multiple notch device would be more time consuming and leave an undesirable margin for error, should the wrong notch be selected. The present invention avoids these problems and eliminates any guesswork by the user.

When preparing to use the intubation device 10 of this invention, the free end 26 of the sheath 24 will be inserted into the distal end 76 of the endotracheal tube 12 until the light bulb 28 is aligned with a sidehole in the tube, or if the tube is beveled, at the proximal edge 78 of the bevel 80. (FIGS. 8-9). At this location, the light 28 is at the end of the endotracheal tube 12 and serves to subsequently identify its location in the patient's trachea 14. The clasp 54 is then secured in the clamped position to prevent relative movement between the sheath 24 and the tube 12.

A special tube stop 82 is provided on the sheath to identify when the light bulb 28 is aligned with the tube's distal end 76. The tube stop 82 may be conveniently moved relative to the sheath 2 until it abuts a fitting 84 at the proximal end 86 of the tube 12, where it is thereafter locked in place. Once locked in place, the tube stop 82 allows the light bulb 28 to consistently and reliably be positioned at the distal end 76 of the tube 12.

Figure 5:
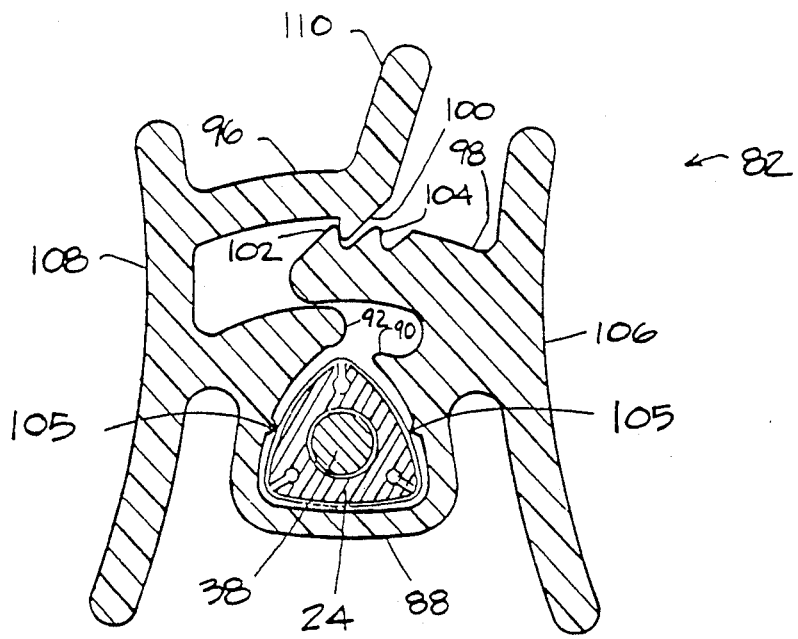
FIG. 5 is a cross-sectional view of a tube stop of the intubation device, taken substantially along line 5—5 of FIG. 2, showing the tube stop in an unsecured condition.
Figure 6:
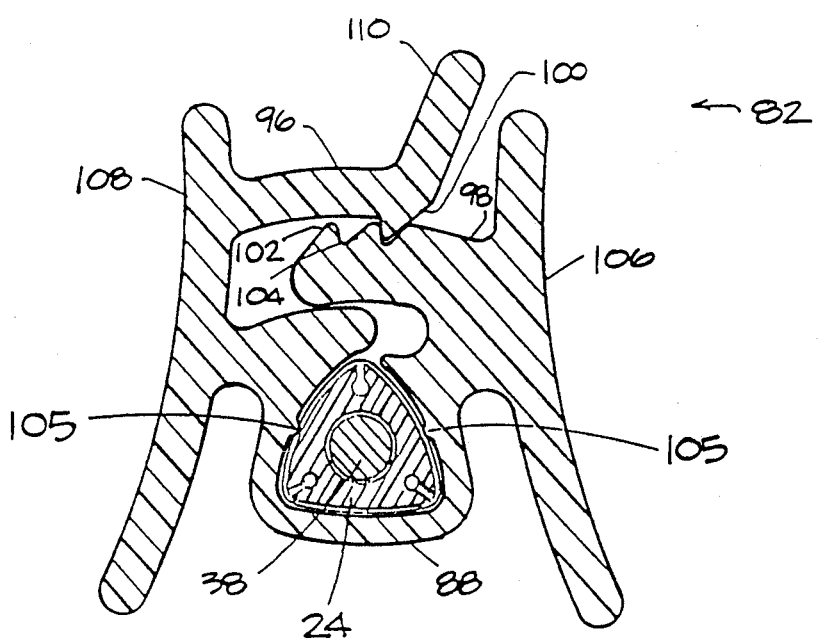
FIG. 6 is another cross-sectional view of the tube stop, similar to FIG. 5, showing the tube stop in a secured condition.

As shown best in FIGS. 5-6, the tube stop 82 comprises a substantially triangular shaped body 8 that fits around the sheath 24, which also is triangular in cross-section. The tube stop 82 includes two integrally formed flaps 90 and 92 that surround the sheath 24. The tube stop 82 also has two overlapping flanges comprising an upper flange 96 and a lower flange 98 that interlock with each other. The upper flange 96 has one downwardly facing positioning tab 100, and the lower flange 98 has two upwardly facing tabs comprising a retaining tab 102 and a locking tab 104. When the positioning tab 100 engages the retaining tab 102, the tube stop 82 is free to slide along the sheath 24. However, when the positioning tab 100 engages the locking tab 104, the tube stop 82 is locked in place on the sheath 24 and will not move. To lock the tube stop 82 onto the sheath 24, the ends 106 and 108 of the flanges 96 and 98 are manually squeezed together to interlock the positioning tab 100 with the locking tab 104. In the locked position, a pair of protrusions 105 on the inner surface of the tube stop's body 88 are compressed against the outer surface of the sheath 24 to enhance clamping force. To unlock the tube stop 82, a lip 110 on the upper flange 96 is lifted to release the positioning tab 100 from the locking tab 104. This allows the positioning tab to engage the retaining tab 102, thereby permitting the tube stop to slide along the sheath 24.

Because of the importance of having the light bulb 28 properly positioned at the tube's distal end 76, a second means of ensuring proper positioning is provided. It comprises reference numerals 112 on the sheath 24 at locations that are 26 and 29 centimeters, respectively, from the free end 26 of the sheath. It is known that virtually all endotracheal tubes have reference markings on their outer surface corresponding to the distance in centimeters from the distal end of the tube. Therefore, by aligning the reference numerals 112 on the sheath 24 with the centimeter markings on the endotracheal tube 12, the location of the light bulb 28 with respect to the distal end 76 of the tube 12 can be visually determined. These reference numerals on the sheath 24, therefore, provide a reliable visual backup to the tube stop 82. This is important when the sheath 24 is inserted into an in-place tube for the purpose of accurately confirming and determining the position of the distal end 76 of the endotracheal tube 12, which should be half-way between the patient's vocal cords 114 and carina 116.

The use of the intubation device 10 of the present invention in conjunction with an endotracheal tube 12, together with other features and advantages of the invention, will now be described. Of course, all intubation procedures must be preceded by adequate suction, oxygenation and ventilation of the patient. Following these routine procedures, the intubation device 10 may be used, with or without a laryngoscope (not shown), to insert the endotracheal tube 12 into the patient's trachea 14. Orotracheal intubation will be described first in conjunction with FIG. 8, followed by nasotracheal intubation in conjunction with FIG. 9.

With the trocar wire 38 in place, the sheath 24 is lubricated and inserted into the distal end 76 of the endotracheal tube 12. When the light bulb 28 is aligned with either the side-hole or proximal edge 78 of the bevel 80 at the distal end 76 of the endotracheal tube 12, the clasp 54 is pivoted from the unclamped position and moved to the clamped position to prevent relative movement between the sheath 24 and the tube 12. If it is anticipated that the intubation device 10 may be needed to check placement of the endotracheal tube 12 at a later time, the tube stop 82 is slideably moved along the sheath 24 until it contacts the fitting 84 at the proximal end 86 of the endotracheal tube 12, where it is thereafter snapped to the locked position. The sheath 24 and tube 12 are then bent at a right angle into the shape of a hockey stick, as shown in FIG. 7, and the slide switch 34 is moved to the "on" position to illuminate the light bulb 28.

If a laryngoscope is used to expose the upper airway anatomy, the illumination from the light bulb 28 will aid in visualizing the airway even further. Under ideal circumstances, visualization of the patient's vocal cords 114 will be possible. Thus, with the end of the endotracheal tube 12 lightly lubricated and the light bulb 28 tested, the user may stand to either the right or left side of the patient, holding the intubation device 10 in the dominant hand. The distal end 76 of the tube 12 may be inserted into the patient's mouth 118 and up against the cheek, with the light bulb 28 illuminated to provide a reference degree of illumination visible through the patient's cheek. The patient's tongue 120 and jaw 122 are then lifted forward and upward, slightly opening the patient's mouth 118. This causes the epiglottis 124 to be lifted up and out of the way of the advancing tube 12. Although the light bulb 28 can be illuminated continuously during this process, if the ambient lighting is extremely bright, it may be helpful to pulse the light bulb 28 with the button switch 36 to improve the perception of the illumination through the patient's skin. Next, the distal end 76 of the endotracheal tube 12 is slid along the tongue 120 until the distal end 76 of the tube 12 "hooks up" the epiglottis 124. As the tip of the tube 12 approaches the glottic opening 126, the transilluminated glow from the light bulb 28 should be seen and should be relatively distinct when the tube tip 76 enters the larynx. The transilluminated glow through the larynx should be bright and circumcised and substantially the same as the reference degree of illumination previously seen through the patient's cheek.

The absence of a distinct transilluminated glow in the larynx indicates that the tube tip 76 is in the esophagus 128 and not the trachea 14. In these circumstances, the tube 12 should be withdrawn slightly and the attempt to enter the larynx should be repeated. In this regard, some users prefer to place the tube tip 76 first in one of the pyriform fossae, since this area is readily transilluminated and provides a further reference point from which to medially direct the tube tip 76 through the glottic opening 126.

In any event, once a proper transilluminated glow is detected in the larynx, the endotracheal tube 12 is advanced slightly and the trocar wire 38 is gradually retracted about 3-4 inches. With the trocar wire 38 retracted, the free end 26 of the sheath 24 and endotracheal tube 12 become pliable and easily conform to the upper airway anatomy. This allows further advancement of the tube 12 into the trachea 14 while minimizing the risk of tracheal wall damage or other trauma.

As the tube 12 and sheath 24 continue to be advanced into the trachea 14, illumination from the light bulb 28 will be visualized through the patient's skin. If desired, the bulb 28 may be pulsed by depressing the button switch 36. The tube 12 will be advanced until illumination of the bulb 28 is visualized in the area of the sternal notch 130, indicating that the distal end 76 of the endotracheal tube 12 is at the desired location half-way between the patient's vocal cords 114 and carina 116. It is noted that the transilluminated glow at the sternal notch 130 should be substantially the same as the reference degree of illumination visualized through the patient's cheek at the start of the intubation process. The tube 12 should be held firmly while the clasp 54 is released, and the sheath 24 thereafter withdrawn from the tube 12. The patient can then be ventilated, the chest auscultated, and the tube 12 anchored in place in the conventional manner.

When using the intubation device 10 of the present invention for nasotracheal intubation, the trocar wire 38 is removed and not used. Removal of the trocar wire 38 allows the sheath 24 to become pliable and flexible, similar to a stylet, for easy insertion into the nasotracheal tube. Thus, the light bulb 28 at the end of the sheath 24 not only provides the necessary transilluminating light, but the flexible yet firm sheath 24 gives support to the tube 12. This helps direct the tube tip 76 anteriorally, particularly when using a directional-tip tube.

The procedure for nasotracheal intubation using the intubation device 10 of the present invention is not very different from the previously described technique for orotracheal intubation. All of the procedures described above are followed to a point just prior to insertion of the tube tip 76 along the tongue 120 and into the epiglottis 124. Thus, the patient is adequately prepared, the tube 12 is clamped to the intubation device 10 and lubricated, and a reference degree of illumination may be visualized through the cheek.

Next, the tube 12 is positioned and slid along the nasal floor or septum 132 to curve around the posterior pharyngeal wall. If a directional-tip tube is used, tension on a string loop (not shown) helps to curve the distal end 76 of the tube 12 around the pharyngeal wall. The light bulb 28 at the sheath's free end 26 can then be illuminated, by either moving the slide switch 34 to the "on" position or by depressing the button switch 36, and the patient's tongue 120 and jaw 122 pulled forward and upward. This movement essentially lifts the epiglottis 124 up and out of the way, similar to the orotracheal technique. Once the tube tip 76 has entered the glottic opening 126 and is in the larynx, the procedures of transillumination and insertion are essentially the same as those described above in connection with orotracheal intubation.

Once the endotracheal tube 12 has been properly placed in the trachea 14, it may be desirable at a later time to recheck its placement. If the endotracheal tube 12 has somehow been moved out of the trachea 14 and into the esophagus 128, or has passed the carina 116 and extended into one of the airways to one of the lungs, serious complications and even death could occur. Therefore, confirmation of tube placement is essential to proper patient care.

To check placement of the endotracheal tube 12 using the intubation device 10 of the present invention, the patient is first suctioned appropriately and hyperventilated with oxygen. With the trocar wire 38 removed, the flexible sheath 24 is lubricated and placed inside the patient's mouth 118 and up against the cheek to check light intensity and establish a reference degree of illumination. The sheath 24 is then inserted into the tube 12, preferably with the slide switch 34 moved to the "on" position and the light bulb 28 illuminated. As the sheath 24 is inserted into the tube 12, a bright glow of illumination should be first seen in the oropharynx. As the sheath 24 is continually advanced, the illumination will diminish as the bulb 28 passes the patient's vocal cords 114, and it will then reappear at the paryngeal prominence. If the tube stop 82 has been previously set, as described above, the sheath 24 will be inserted until the tube stop 82 abuts the fitting 84 at the proximal end 86 of the tube 12. At this point, the glow should be visible at the sternal notch 130, thereby confirming proper placement of the tube 12 half-way between the patient's vocal cords 114 and carina 116. If the glow does not appear, or if the illumination is not in the proper location, then the tube 12 should be adjusted appropriately. The sheath 24 can then be removed and ventilation continued. If the tube stop 82 has not been set or if it has been released from its initial position on the sheath 24, then the user should align the reference markings 112 on the sheath 24 with the corresponding centimeter markings on the endotracheal tube 12.

While a particular form of the invention has been illustrated and described, it will be apparent that various modifications can be made without departing from the spirit and scope of the invention. There it is not intended that the invention be limited, except as by the appended claims.

We claim:

1. An intubation device for use with an endotracheal tube, the endotracheal tube having a distal end for insertion into a patient's trachea and a proximal end outside the patient, the device comprising:
   (a) a housing;
   (b) a flexible sheath having one end connected to the housing and a free end extending away from the housing, the sheath being adapted to fit within the endotracheal tube;
   (c) light means at the end of the sheath's free end for selectively providing illumination; and
   (d) tube clamp means for releasably securing the endotracheal tube to the housing.

2. The intubation device of claim 1, wherein the tube clamp means comprises:
   (a) a tube holder connected to the housing having a tube receiving portion facing the endotracheal tube;
   (b) a clasp releasably connected tot he tube holder for clamping the endotracheal tue down against the tube receiving portion of the tube holder; and
   (c) connecting means for releasably connecting the clasp to the tube holder when the endotracheal tube has been clamped down against the tube receiving portion of the tube holder.

3. The intubation device of claim 2, further comprising a resilient, flexible material positioned over the tube receiving portion of the tube holder for receiving the endotracheal tube, whereby the clasp clamps the endotracheal tube down against the flexible material and the tube receiving portion of the tube holder.

4. The intubation device of claim 3, wherein the flexible material includes a friction enhanced surface for preventing movement between the tube clamp means and the endotracheal tube when the clasp is connected to the tube holder by the connecting means.

5. The intubation device of claim 3, wherein the flexible material comprises a resilient, flexible band positioned over the tube receiving portion for receiving the endotracheal tube, wherein a first end of the band is connected to the tube receiving portion, with at least an intermediate portion of the band being spaced from the tube receiving portion.

6. The intubation device of claim 5, wherein the flexible band is made of metal and further includes a friction enhanced surface comprising protrusions adapted to bite into the outer surface of the endotracheal tube.

7. The intubation device of claim 5, wherein a second end of the flexible band opposite the first end is adapted to urge against the clasp and to rapidly move the clasp away from the tube holder when the clasp is disconnected from the tube holder.

8. The intubation device of claim 3, wherein the connecting means comprises a single position latching mechanism.

9. The intubation device of claim 8, wherein the single position latching mechanism comprises a single notch on the tube holder that is engaged by a finger on the clasp.

10. The intubation device of claim 2, wherein the sheath is connected to the housing at an angle such that a portion of the sheath that overlies the tube holder is normally spaced from the tube holder.

11. The intubation device of claim 1, further comprising stiffening means for insertion inside the sheath.

12. The intubation device of claim 11, wherein the stiffening means comprising a trocar wire having an inserted end for insertion inside the sheath and a free end remaining outside the sheath.

13. The intubation device of claim 12, further comprising means on the housing and the wire for preventing rotation of the wire with respect to the sheath.

14. The intubation device of claim 12, wherein the wire is comprised of a ductile or malleable material such that the wire may be bent and maintained at varying angles.

15. The intubation device of claim 12, wherein the sheath is made of a material having a low coefficient of friction to facilitate the insertion and withdrawal of the wire from the sheath.

16. The intubation device of claim 12, wherein the trocar wire is coated with a material having a low coefficient of friction to facilitate the insertion and withdrawal of the wire from the sheath.

17. The intubation device of claim 1, further comprising tube stop means for positioning on the sheath, such that when the sheath has been inserted into the endotracheal tube to a predetermined location, the tube stop means may be secured to the sheath in abutting contact with the proximal end of the endotracheal tube.

18. The intubation device of claim 1, further comprising means for determining when the light means is at the distal end of the endotracheal tube, comprising reference markings on the endotracheal tube which align with and match counterpart reference markings on the sheath or the housing.

19. The intubation device of claim 1, wherein the light means comprises a light source at the end of the sheath's free end, and whereni a portion of the illumination created by the light source is directed to one side of the sheath.

20. The intubation device of claim 19, wherein the light source includes a reflector to reflect illumination to one side of the sheath.

21. The intubation device of claim 20, wherein the light source further includes a lens to focus illumination from the light source in a direction substantially parallel to the longitudinal axis of the sheath.

22. The intubation device of claim 1, wherein the light means includes a lens to focus illumination from the light source in a direction substantially parallel to the longitudinal axis of the sheath.

23. The intubation device of claim 1, further comprising switch means for controlling illumination of the light means.

24. The intubation device of claim 23, wherein the switch means comprises:
   (a) a first switch movable to an on position for turning the light means on and moveable to an off position for turning the light means off; and
   (b) a second switch that may be actuated for turning the light means on when the first switch is in the off position and for turning the light means off when the first switch is in the on position.

25. A device for checking the placement of an endotracheal tube in a patient's trachea, wherein the endotracheal tube has a distal end for insertion into the patient's trachea and a proximal end outside the patient, the device comprising:
(a) a housing;
(b) a flexible sheath having one end connected to the housing and a free end extending away form the housing, the sheath being adapted to fit within the endotracheal tube;
(c) light means at the end of the sheath's free end for selectively providing illumination; and
(d) tube stop means for positioning on the sheath in abutting contact with the proximal end of the endotracheal tube, the tube stop means being secured to the sheath in said abutting contact when the light means is substantially at the distal end of the endotracheal tube, whereby subsequent checking of endotracheal tube placement in the patient's trachea is enabled by reinserting the sheath into the endotracheal tube until the tube stop means abuts the proximal end of the endotracheal tube.

26. The intubation device of claim 25, wherein the tube stop means comprises a body portion surrounding the sheath, the body portion having an upper flange and a lower flange adapted to overlap each other, the upper flange having a positioning tab and the lower flange having a retaining tab and locking tab, such that when the positioning tab is engaged with the retaining tab the tube stop means is retained but free to slide along the sheath, and such that when the positioning tab is engaged with the locking tab the tube stop means is secured against sliding movement on the sheath.

27. A method of intubating a patient with an endotracheal tube using a device having a flexible sheath with one end connected to a housing and a free end extending away from the housing, wherein the endotracheal tube has a distal end for insertion into the patient's trachea and a proximal end outside the patient, the method comprising the stops of:
(a) inserting the sheath into the endotracheal tube until the free end of the sheath is substantially at the distal end of the endotracheal tube;
(b) clamping the endotracheal tube to the sheath to prevent relative movement between the endotracheal tube and the sheath; and
(c) inserting the distal end of the endotracheal tube into the patient's trachea.

28. The method of claim 27, wherein the device includes light means at the free end of the sheath, further comprising the steps of:
(a) illuminating the light means;
(b) determining the location of the distal end of the endotracheal tube in the patient by visualizing illumination form the light means through the patient'skin; and
(c) moving the endotracheal tube relative to the patient's trachea until illumination from the light means is visible through the patient's skin in the area of the sternal notch to thereby ensure proper placement of the endotracheal tube in the trachea between the patient's vocal cords and carina.

29. The method of claim 28 further comprising the step of marking a reference point on the sheath corresponding to the proximal end of the endotracheal tube after the endotracheal tube has been secured to the sheath.

30. The method of claim 29 further comprising the step of releasing the endotracheal tube from the sheath and withdrawing the sheath from the endotracheal tube.

31. The method of claim 30 further comprising the steps of:
(a) reinserting the sheath into the endotracheal tube until the reference point on the sheath aligns with the proximal end of the endotracheal tube; and
(b) verifying the proper placement of the endotracheal tube in the trachea by illuminating the light means and visualizing illumination through the patient's skin in the area of the sternal notch.

32. The method of claim 27 further comprising the step of:
(a) initially inserting a stiffening member inside the sheath to provide added stiffness to the sheath; and
(b) bending the endotracheal tube, after the sheath and stiffening member have been inserted into the endotracheal tube, to form an angle at the distal end of the endotracheal tube to facilitate insertion of the endotracheal tube into the patient's trachea.

33. The method of claim 32, further comprising the step of preventing rotation of the stiffening member with respect to the sheath after the stiffening member has been inserted within the sheath.

34. A method of intubating a patient with an endotracheal tube using a device having a flexible sheath with one end connected to a housing and a free end extending away form the housing, and light means at the sheath's free end for selectively providing illumination, wherein the endotracheal tube has a distal end for insertion into the patient's trachea and a proximal end outside the patient, the method comprising the steps of:
(a) inserting the sheath into the endotracheal tube until the free end of the sheath is substantially at the distal end of the endotracheal tube;
(b) clamping the endotracheal tube to the sheath to prevent relative movement between the endotracheal tube and the sheath;
(c) placing the distal end of the endotracheal tube in the patient's mouth and up against the cheek prior to inserting the endotracheal tube into the trachea;
(d) illuminating the light means to provide a reference degree of illumination visible through the patient's cheek;
(e) inserting the distal end of the endotracheal tube into the patient's trachea; and
(f) stopping insertion of the endotracheal tube when illumination form the light means that is substantially the same as the reference degree of illumination visible through the patient's cheek is visible through the patient's skin in the area of the patient's sternal notch.

* * * * *

UNITED STATES PATENT AND TRADEMARK OFFICE
CERTIFICATE OF CORRECTION

PATENT NO. : 5,163,941
DATED : November 17, 1992
INVENTOR(S) : Geoffrey C. Garth and Charles A. Patterson It is certified that error appears in the above-indentified patent and that said Letters Patent is hereby corrected as shown below:

| | |
|---|---|
| Col. 8, ln. 68: | device 1 to facilitate (should be) device 10 to facilitate |
| Col. 9, ln. 48: | sheath to identify (should be) sheath 24 to identify |
| Col. 9, ln. 51: | to the sheath 2 (should be) to the sheath 24 |
| Col. 9, ln. 57: | triangular shaped body 8 (should be) triangular shaped body 88 |
| Col. 12, ln. 57: | at the paryngeal prominence (should be) at the laryngeal prominence |
| Col. 13, ln. 8: | There it is (should be) Therefore, it is |
| Col. 14, ln. 43: | and whereni (should be) and wherein |
| Col. 15, ln. 8: | away form (should be) away from |
| Col. 15, ln. 57: | illumination form (should be) illumination from |
| Col. 16, ln. 37: | away form (should be) away from |

UNITED STATES PATENT AND TRADEMARK OFFICE
CERTIFICATE OF CORRECTION

PATENT NO. : 5,163,941
DATED : November 17, 1992
INVENTOR(S) : Geoffrey C. Garth and Charles A. Patterson It is certified that error appears in the above-indentified patent and that said Letters Patent is hereby corrected as shown below:

Col. 16, ln. 57: illumination form (should be) illumination from

Signed and Sealed this

Fourth Day of January, 1994

Attest:

BRUCE LEHMAN

Attesting Officer

Commissioner of Patents and Trademarks